(12) United States Patent
West et al.

(10) Patent No.: US 6,500,947 B1
(45) Date of Patent: Dec. 31, 2002

(54) SUPERABSORBENT POLYMER

(75) Inventors: Hugh West, Seattle, WA (US); John A. Westland, Auburn, WA (US)

(73) Assignee: Weyerhaeuser Company, Federal Way, WA (US)

( * ) Notice: Subject to any disclaimer, the term of this patent is extended or adjusted under 35 U.S.C. 154(b) by 0 days.

(21) Appl. No.: 09/939,182

(22) Filed: Aug. 24, 2001

(51) Int. Cl.$^7$ .................................................. C07H 1/00
(52) U.S. Cl. ..................... 536/123.1; 536/30; 536/56; 536/57
(58) Field of Search .............................. 536/36, 56, 57, 536/123.1

(56) References Cited

U.S. PATENT DOCUMENTS

| | | | |
|---|---|---|---|
| 3,075,963 A | 1/1963 | Hiatt et al. | |
| 3,589,364 A | 6/1971 | Dean et al. | |
| 3,673,110 A | 6/1972 | Edwards | |
| 3,702,843 A | 11/1972 | Schweiger | |
| 3,723,413 A | 3/1973 | Chatterjee et al. | |
| 3,804,092 A | 4/1974 | Tunc | |
| 3,858,585 A | 1/1975 | Chatterjee | |
| 4,035,569 A | 7/1977 | Schweiger | |
| 4,064,342 A | 12/1977 | Saika et al. | |
| 4,102,340 A | 7/1978 | Mesek et al. | |
| 4,138,535 A | 2/1979 | Schweiger | |
| 4,141,746 A | 2/1979 | Schweiger | |
| 4,187,342 A | 2/1980 | Holst et al. | |
| 4,242,506 A | 12/1980 | Schweiger | |
| 4,256,877 A | 3/1981 | Karlsson et al. | |
| 4,294,731 A | 10/1981 | Allen | |
| 4,340,731 A | 7/1982 | Colombo et al. | |
| 4,368,323 A | 1/1983 | James | |
| 4,418,524 A | 12/1983 | Ito et al. | |
| 4,480,091 A | 10/1984 | Brewer | |
| 4,584,370 A | 4/1986 | Taguchi et al. | |
| 4,689,408 A | 8/1987 | Gelman et al. | |
| 4,708,771 A | 11/1987 | Beaulieu | |
| 4,734,478 A | 3/1988 | Tsubakimoto et al. | |
| 4,758,617 A | 7/1988 | Tanioku et al. | |
| 4,801,699 A | 1/1989 | Jobe et al. | |
| 4,929,722 A | 5/1990 | Partain, III et al. | |
| 4,952,550 A | 8/1990 | Wallach et al. | |
| 4,981,959 A | 1/1991 | Diamantoglou | |
| 4,981,960 A | 1/1991 | Diamantoglou | |
| 4,997,935 A | 3/1991 | Diamantoglou | |
| 5,008,385 A | 4/1991 | Diamantoglou | |
| 5,053,029 A | * 10/1991 | Yang ..................... 604/385.1 | |
| 5,089,089 A | 2/1992 | Beaulieu | |
| 5,093,486 A | 3/1992 | Diamantoglou | |
| 5,093,488 A | 3/1992 | Diamantoglou | |
| 5,093,489 A | 3/1992 | Diamantoglou | |
| 5,116,921 A | 5/1992 | Hsieh | |
| 5,137,537 A | 8/1992 | Herron et al. | |
| 5,144,021 A | 9/1992 | Arie et al. | |
| 5,149,335 A | 9/1992 | Kellenberger et al. | |
| 5,167,654 A | * 12/1992 | Yang ..................... 604/385.1 | |
| 5,247,072 A | 9/1993 | Ning et al. | |
| 5,324,823 A | 6/1994 | Asakawa et al. | |
| 5,371,207 A | 12/1994 | Zhuang | |
| 5,378,826 A | 1/1995 | Hoppe et al. | |
| 5,405,953 A | 4/1995 | Banker et al. | |
| 5,470,964 A | 11/1995 | Qin | |
| 5,476,459 A | * 12/1995 | Yang ..................... 604/385.1 | |
| 5,498,705 A | 3/1996 | Oin | |
| 5,502,082 A | 3/1996 | Unger et al. | |
| 5,541,255 A | 7/1996 | Kozulic | |
| 5,550,189 A | 8/1996 | Qin et al. | |
| 5,561,114 A | 10/1996 | Komai et al. | |
| 5,599,916 A | 2/1997 | Dutkiewicz et al. | |
| 5,612,321 A | 3/1997 | Nguyen | |
| 5,703,225 A | 12/1997 | Shet et al. | |
| 5,731,259 A | 3/1998 | Palumbo et al. | |
| 5,734,025 A | 3/1998 | Komai et al. | |
| 5,739,316 A | 4/1998 | Beer et al. | |
| 5,760,200 A | 6/1998 | Miller et al. | |
| 5,770,583 A | 6/1998 | Haslwanter et al. | |
| 5,780,616 A | 7/1998 | Fornasari et al. | |
| 5,792,855 A | 8/1998 | Yonemura et al. | |
| 5,837,627 A | * 11/1998 | Halabisky et al. ........... 442/385 | |
| 5,854,030 A | 12/1998 | Dordick | |
| 5,912,276 A | * 6/1999 | Adamski et al. ............... 521/64 | |
| 5,948,829 A | 9/1999 | Wallajapet et al. | |
| 5,951,910 A | 9/1999 | Skaggs et al. | |
| 5,986,087 A | 11/1999 | Schrell et al. | |
| 5,998,606 A | 12/1999 | Grandics | |
| 6,015,936 A | 1/2000 | Takai et al. | |
| 6,020,536 A | 2/2000 | Osterdahl et al. | |
| 6,063,982 A | 5/2000 | Martin et al. | |

(List continued on next page.)

FOREIGN PATENT DOCUMENTS

| | | |
|---|---|---|
| CA | 731 146 | 3/1966 |
| CA | 2 072 918 A1 | 8/1993 |
| DE | 40 21 049 A1 | 2/1992 |
| EP | 0 023 384 A1 | 2/1981 |
| EP | 0 566 118 A1 | 10/1993 |
| WO | WO 96/15137 A1 | 5/1996 |
| WO | WO 99/20318 A2 | 4/1999 |
| WO | WO 00/27886 A1 | 5/2000 |
| WO | WO 00/47628 A2 | 8/2000 |

OTHER PUBLICATIONS

"Cellulose Chemistry and Its Applications," Halstead Press, John Wiley and Sons, 1985, p. 350.

(List continued on next page.)

Primary Examiner—James O. Wilson
Assistant Examiner—Patrick Lewis
(74) Attorney, Agent, or Firm—Christensen O'Connor Johnson Kindness PLLC

(57) ABSTRACT

The present invention provides a polymer derived from a cellulosic, lignocellulosic, or polysaccharide material having superabsorbent properties. Methods for making the polymer and personal care absorbent products that incorporated the polymer are also provided.

7 Claims, 3 Drawing Sheets

U.S. PATENT DOCUMENTS

| | | | |
|---|---|---|---|
| 6,083,211 | A | 7/2000 | DesMarais |
| 6,107,356 | A | 8/2000 | DesMarais |
| 6,107,538 | A | 8/2000 | Young et al. |
| 6,121,409 | A | 9/2000 | Mitchell et al. |
| 6,135,987 | A | 10/2000 | Tsai et al. |
| 6,156,492 | A | 12/2000 | Kobayashi et al. |
| 6,293,935 | B1 * | 9/2001 | Kimura et al. ............. 604/387 |

OTHER PUBLICATIONS

Arai, K. and H. Goda, "Crosslinked Sodium Cellulose Sulfate as Highly Absorbent Material," Translation of *Sen–I–Gakkaishi* 49(9):482–485, 1993.

Balser, K., et al., "Cellulose Esters", *Ullmann's Encyclopedia of Industrial Chemistry, vol. A5*, 5th Rev. Ed., VCH, New York, 1986, pp. 419, 431–437.

Banyai, B.E., et al., "Cellulosic Derivatives as Biodegradable Absorbent Polymers for Nonwovens," *Insight 1992*, Section 4–1 through 4–6.

Podlas, T.J., "Internally Crosslinked Carboxymethylcellulose Fibers for Absorbent Nonwovens Applications," *Nonwoven Technology—Challenges and Achievements*, Technical Symposium, Atlanta, Georgia, Mar. 2–3, 1976, pp. 25–39.

Schweiger, R.G., "New Cellulose Sulfate Derivatives and Applications," *Carbohydrate Research* 70(2):185–198, May 1979.

Sjöström, E., *Wood Chemistry Fundamentals and Applications*, 2d ed., Academic Press, San Diego, CA, 1993, pp. 210–211.

* cited by examiner

SUPERABSORBENT POLYMER

FIELD OF THE INVENTION

The present invention relates to a modified cellulosic, lignocellulose or polysaccharide having superabsorbent properties and, more particularly, to a sulfated cellulosic, lignocellulose or polysaccharide.

BACKGROUND OF THE INVENTION

Personal care absorbent products, such as infant diapers, adult incontinent pads, and feminine care products, typically contain an absorbent core that includes superabsorbent polymer particles distributed within a fibrous matrix. Superabsorbents are water-swellable, generally water-insoluble absorbent materials having a high absorbent capacity for body fluids. The superabsorbent polymers (SAP's) in common use are mostly derived from acrylic acid, which is itself derived from oil, a non-renewable raw material. Acrylic acid polymers and SAP's are generally recognized as not being biodegradable. Despite their wide use, some segments of the absorbent products market are concerned about the use of non-renewable oil derived materials and their non-biodegradable nature. Acrylic acid based polymers also comprise a meaningful portion of the cost structure of diapers and incontinent pads. Users of SAP are interested in lower cost SAP's. The high cost derives in part from the cost structure for the manufacture of acrylic acid which, in turn, depends upon the fluctuating price of oil. Also, when diapers are discarded after use they normally contain considerably less than their maximum or theoretical content of body fluids. In other words, in terms of their fluid holding capacity, they are "over-designed". This "over-design" constitutes an inefficiency in the use of SAP. The inefficiency results in part from the fact that SAP's are designed to have high gel strength (as demonstrated by high absorbency under load or AUL). The high gel strength (upon swelling) of currently used SAP particles helps them to retain a lot of void space between particles, which is helpful for rapid fluid uptake. However, this high "void volume" simultaneously results in there being a lot of interstitial (between particle) liquid in the product in the saturated state. When there is a lot of interstitial liquid the "rewet" value or "wet feeling" of an absorbent product is compromised.

In personal care absorbent products, U.S. southern pine fluff pulp is commonly used in conjunction with the SAP. This fluff is recognized worldwide as the preferred fiber for absorbent products. The preference is based on the fluff pulp's advantageous high fiber length (about 2.8 mm) and its relative ease of processing from a wetlaid pulp sheet to an airlaid web. Fluff pulp is also made from renewable, and biodegradable cellulose pulp fibers. Compared to SAP, these fibers are inexpensive on a per mass basis but tend to be more expensive on a per unit of liquid held basis. These fluff pulp fibers mostly absorb within the interstices between fibers. For this reason, a fibrous matrix readily releases acquired liquid on application of pressure. The tendency to release acquired liquid can result in significant skin wetness during use of an absorbent product that includes a core formed exclusively from cellulosic fibers. Such products also tend to leak acquired liquid because liquid is not effectively retained in such a fibrous absorbent core.

A need therefore exists for a superabsorbent material that is simultaneously made from a biodegradable renewable resource like cellulose or other lignocellulosic or polysaccharide, that is inexpensive, and that has a low void volume when saturated. In this way the superabsorber can be used in absorbent product designs that are efficient such that they can be used closer to their theoretical capacity without feeling wet to the wearer. These and other objects are accomplished by the invention set forth below.

SUMMARY OF THE INVENTION

In one aspect, the present invention provides a superabsorbent polymer. The polymer of the invention is a modified cellulose, modified lignocellulose, or modified polysaccharide having superabsorbent properties. The modified polymer is a sulfated polymer. In one embodiment the polymer is a sulfated cellulose; in another embodiment, a sulfated lignocellulose; and in another embodiment, a sulfated polysaccharide. The polymer of the invention is a water-swellable, water-insoluble polymer having a high liquid absorption capacity and a low free liquid value. In one embodiment, the polymer has a liquid absorption capacity greater than about 20 g/g. In another embodiment, the polymer has a free liquid value of less than about 40 percent by weight based on the total amount of liquid absorbed. In a further embodiment, the polymer has a free liquid value of less than about 30 percent by weight based on the total amount of liquid absorbed. In one embodiment, the modified polymer is a crosslinked polymer.

In other aspects of the invention, methods for making the superabsorbent polymer and absorbent products that incorporate the superabsorbent polymer are provided.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
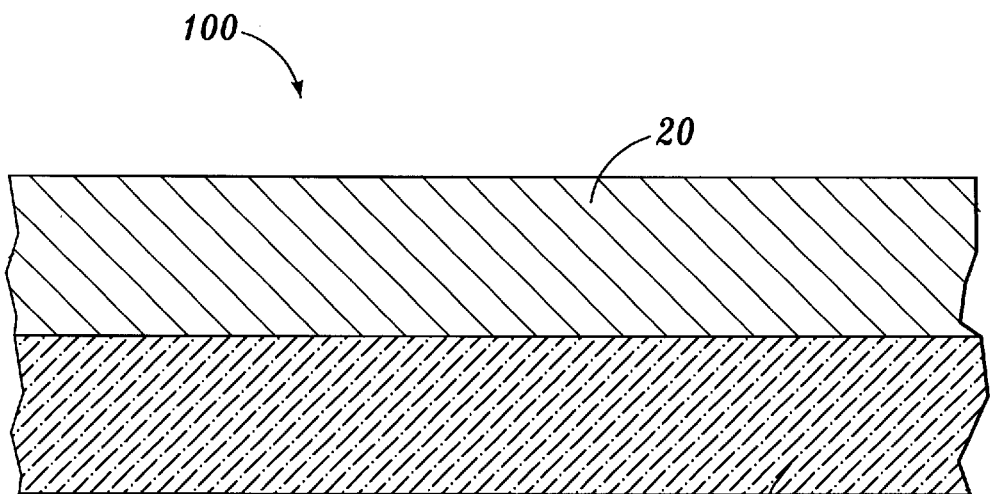
FIG. 1 is a cross sectional view of an absorbent construct incorporating a representative polymer of the invention and having an acquisition layer.

In one aspect, the present invention provides a superabsorbent polymer. The polymer of the invention is a modified cellulose, modified lignocellulose, or modified polysaccharide having superabsorbent properties. The modified polymer is a sulfated polymer. In one embodiment the polymer is a sulfated cellulose; in another embodiment, a sulfated lignocellulose; and in another embodiment, a sulfated polysaccharide.

The polymer of the invention is a water-swellable, water-insoluble polymer having a high liquid absorption capacity. Water swellability is imparted to the polymer through sulfation. The polymer has a degree of sulfate group substitution effective to provide advantageous water swellability. The polymer has a liquid absorption capacity that is increased compared to unmodified fluff pulp fibers. In one embodiment, the polymer has a liquid absorption capacity greater than about 20 g/g.

Cellulosic fibers suitable for use in forming the modified cellulose polymer of the present invention are substantially water-insoluble and not highly water-swellable. After sulfation in accordance with the present invention, the resulting modified polymer has the desired absorbency characteristics, is water-swellable and water-insoluble.

The polymer of the invention is substantially insoluble in water. As used herein, a material will be considered to be water-soluble when it substantially dissolves in excess water to form a solution, losing its form and becoming essentially evenly disbursed throughout a water solution.

The polymer of the invention is a water-swellable, water-insoluble polymer. As used herein, the term "water-swellable, water-insoluble polymer" refers to a polymer that, when exposed to an excess of an aqueous medium (e.g., bodily fluids such as urine or blood, water, synthetic urine, or 1 weight percent solution of sodium chloride in water), swells to an equilibrium volume but does not dissolve into solution.

In addition to having a high liquid absorption capacity, the polymer of the invention has a low free liquid value. As used herein, the term "free liquid value" refers to the amount of liquid that is present in a material that is free and can be readily expelled from the material. The free liquid value relates to the structure of a material. Materials having high void volumes (e.g., large interstitial spaces) will have relatively high free liquid values, and materials having lesser void volumes and smaller interstitial spaces will have relatively low free liquid values. Materials that include conventional superabsorbent polymers, which are substantially spherical in shape and have been designed to have high gel strength, have relatively large void volumes and therefore retain relatively greater amounts of free liquid. Such materials are in contrast to materials that include the polymer of the invention that are characterized as having small void volumes and retain relatively lesser amounts of free liquid. The difference in free liquid reflects the structure of the two absorbent materials. Packing of conventional substantially spherical polymers results in interstitial spaces capable of retaining relatively greater amount of free liquid. The polymer of the invention packs without forming as great interstitial spaces and, consequently, relatively less free liquid is retained.

As used herein, the term "free liquid value" is defined as the percentage of liquid absorbed by a material that can be subsequently expelled from the material on centrifugation. Free liquid value is determined by allowing a material to swell in the liquid absorbing its maximum amount of that liquid, followed by centrifuging the liquid-swelled material to expel free liquid. The difference in weight of the material after initial swelling and the weight of the material after centrifugation to remove free liquid divided by the material weight after initial swelling is the percentage of free liquid absorbed by the material and is the free liquid value. Free liquid value is determined as described in Example 3. In one embodiment, the polymer of the invention has a free liquid value of less than about 40 percent by weight based on the total amount of liquid absorbed. In another embodiment, the polymer has a free liquid value of less than about 30 percent by weight based on the total amount of liquid absorbed. Free liquid values for representative polymers of the invention are described in Table 4 in Example 4.

In one embodiment, cellulosic fibers are a starting material for preparing the polymer of the invention. Although available from other sources, suitable cellulosic fibers are derived primarily from wood pulp. Suitable wood pulp fibers for use with the invention can be obtained from well-known chemical processes such as the kraft and sulfite processes, with or without subsequent bleaching. Pulp fibers can also be processed by thermomechanical, chemithermomechanical methods, or combinations thereof. Caustic extractive pulp such as TRUCELL, commercially available from Weyerhaeuser Company, is also a suitable wood pulp fiber. A preferred pulp fiber is produced by chemical methods. Ground wood fibers, recycled or secondary wood pulp fibers, and bleached and unbleached wood pulp fibers can be used. Softwoods and hardwoods can be used. Details of the selection of wood pulp fibers are well-known to those skilled in the art. These fibers are commercially available from a number of companies, including Weyerhaeuser Company, the assignee of the present invention. For example, suitable cellulosic fibers produced from southern pine that are usable with the present invention are available from Weyerhaeuser Company under the designations CF416, NF405, PL416, FR416, and NB416. In one embodiment, the cellulosic fiber useful in making the polymer of the invention is a southern pine fiber commercially available from Weyerhaeuser Company under the designation NB416. In other embodiments, the cellulosic fiber can be selected from among a northern softwood fiber, a eucalyptus fiber, a rye grass fiber, and a cotton fiber.

Cellulosic fibers having a wide range of degree of polymerization are suitable for forming the polymer of the invention. In one embodiment, the cellulosic fiber has a relatively high degree of polymerization, greater than about 1000, and in another embodiment, about 1500.

In one embodiment, the polymer of the invention is a sulfated cellulose polymer. As used herein, "sulfated cellulose" refers to cellulose that have been sulfated by reaction with a sulfating agent. It will be appreciated that the term "sulfated cellulose" includes free acid and salt forms of sulfated cellulose. Suitable metal salts include sodium, potassium, and lithium salt, among others. A sulfated cellulose polymer can be produced by reacting a sulfating agent with a hydroxyl group of the cellulose to provide a cellulose sulfate ester (i.e., a carbon-to-oxygen-to-sulfur ester). The sulfated cellulose polymer formed in accordance with the present invention differs from other sulfur-containing cellulosic compounds in which the sulfur atom is attached directly to a carbon atom on the cellulose chain as, for example, in the case of sulfonated cellulose; or cellulosic compounds in which the sulfate sulfur atom is attached indirectly to a carbon atom on the cellulose chain as, for example, in the case of cellulose alkyl sulfonates.

The sulfated cellulose polymer of the invention can be characterized as having an average degree of sulfate group substitution of from about 0.1 to about 2.0. In one embodiment, the sulfated cellulose has an average degree of sulfate group substitution of from about 0.2 to about 1.0. In another embodiment, the sulfated cellulose has an average degree of sulfate group substitution of from about 0.3 to about 0.5. As used herein, the "average degree of sulfate group substitution" refers to the average number of moles of sulfate groups per mole of glucose unit in the polymer. It will be appreciated that the polymers formed in accordance with the present invention include a distribution of sulfate modified polymers having an average degree of sulfate substitution as noted above.

The polymer of the invention is a sulfated polymer. In one embodiment, the polymer is derived from cellulosic fibers. Sulfated cellulosic fibers can be made by reacting cellulosic fibers (e.g., cellulosic fibers that are crosslinked or noncrosslinked) with a sulfating agent. Suitable sulfating agents include concentrated sulfuric acid (95–98%), fuming sulfuric acid (oleum), sulfur trioxide and related complexes including sulfur trioxide/dimethylformamide and sulfur trioxide/pyridine complexes, and chlorosulfonic acid, among others. In one embodiment, the sulfating agent is concentrated sulfuric acid.

The sulfating agent is preferably applied to the fibers as a solution in an organic solvent. Suitable organic solvents include alcohols, pyridine, dimethylformamide, acetic acid including glacial acetic acid, and dioxane. In one embodiment, the organic solvent is an alcohol having up to about 6 carbon atoms. Suitable alcohols include methanol, ethanol, n-propanol, isopropanol, n-butanol, isobutanol, s-butanol, pentanols, and hexanols. In one embodiment, the alcohol is selected from among isopropanol and isobutanol.

The molar ratio of sulfuric acid to alcohol in the solution can be varied from about 1:1 to about 4:1. In one embodiment, the molar ratio of sulfuric acid to alcohol is about 2.4:1, for example, an 80:20 (weight/weight) solution of sulfuric acid in isopropanol. The weight ratio of sulfuric acid to cellulosic fibers in the sulfation reaction can be varied from about 5:1 to about 30:1. At low sulfuric acid ratios the reaction is slow and incomplete and at high sulfuric acid ratios significant cellulose polymer degradation can occur. In one embodiment, the weight ratio of sulfuric acid to pulp fiber is from about 10:1 to about 25:1. In another embodiment, the weight ratio of sulfuric acid to pulp fiber is about 24:1.

Highly acidic aqueous environments readily degrade cellulose fibers. It has been reported that concentrated sulfuric acid cannot be used to prepare sulfated cellulose because treating cellulose with sulfuric acid results in a soluble product formed from acid hydrolysis of the cellulose backbone by the sulfuric acid. See, WO 96/15137. However, a water-soluble cellulose sulfate has been reportedly prepared from an activated cellulose (20 to 30% water) by direct action of aqueous sulfuric acid or sulfuric acid dissolved in a volatile organic solvent such as toluene, carbon tetrachloride, or a lower alkanol. "Cellulose Chemistry and Its Applications", Ed. T. P. Nevell and S. H. Zeronian, Halstead Press, John Wiley and Sons, 1985, page 350.

Despite the well-known degradation of cellulose in aqueous acidic solutions, the present invention provides methods for making sulfated cellulose polymers without significant cellulose hydrolysis. In the methods of the invention, cellulose degradation (i.e., degree of polymerization reduction) is substantially avoided by treating cellulose fibers with a sulfating agent in a nonaqueous environment and/or at low temperature (e.g., at or below about 4° C.). To further protect against cellulose degradation (e.g., hydrolysis), a stabilizing agent or dehydrating agent to absorb water, including water formed during the sulfation reaction, can be added to the sulfating reaction mixture. Suitable stabilizing or dehydrating agents include, for example, sulfur trioxide, magnesium sulfate, acetic anhydride, and molecular sieves. In one embodiment, cellulosic fibers are reacted with the sulfating agent at a temperature of about 4° C. and both the cellulosic fibers and the sulfating agent are cooled to about 4° C. prior to reaction. In another embodiment, cellulosic fibers, including cooled fibers, are reacted with the sulfating agent in the presence of a dehydrating agent.

Depending upon the extent of sulfation desired, the fibers and sulfating agent are reacted for a period of time of from about 10 to about 300 minutes. Following this reaction period and prior to neutralizing the resulting sulfated fibers, the sulfated fibers are separated from excess sulfating agent. In one embodiment, the sulfated fibers are washed with an alcohol prior to neutralization.

Prior to further processing the sulfated cellulosic fibers (e.g., crosslinking) to provide the polymer of the invention, the fibers can be at least partially neutralized with a neutralizing agent. The neutralizing agent is suitably soluble in the sulfation solvent. In one embodiment, the neutralizing agent is a base such as, for example, an alkaline base (e.g., lithium, potassium, sodium or calcium hydroxide; lithium, potassium, or sodium acetate). Alternatively, the neutralizing agent can include a multivalent metal salt. Suitable metal salts include cerium, magnesium, calcium, zirconium, and aluminum salts such as ammonium cerium nitrate, magnesium sulfate, magnesium chloride, calcium chloride, zirconium chloride, aluminum chloride, and aluminum sulfate, among others. The use of multivalent metal salts as neutralizing agents also offers the advantage of intrafiber crosslinking. Thus, through the use of a multivalent metal salt, the sulfated cellulosic can be partially neutralized and partially crosslinked. Fibers so treated can be further crosslinked with other crosslinking agents including those described above.

The extent of fiber sulfation is dependent on a number of reaction conditions including reaction time. For example, in a series of representative sulfation reactions, a 25 minute reaction time provided a fiber that included about 3.8 percent by weight sulfur; a 35 minute reaction time provided a fiber that included about 4.9 percent by weight sulfur; and a 45 minute reaction time provided a fiber that included about 6.4 percent by weight sulfur. However, in these experiments, the extended sulfation reaction time had an adverse effect on fiber length (i.e., cellulose hydrolysis occurred under the prolonged reaction conditions). In viscosity experiments, the sulfated fibers produced by the 25 and 35 minute reaction conditions provide cellulose solutions classified as having a Gardner-Holt bubble tube H viscosity (i.e., about 200 Centistokes), while the sulfated fibers produced by the 45 minute reaction provided cellulose solutions classified as having C viscosity (i.e., about 85 Centistokes). The results indicate that at extended reaction times, significant fiber degradation can occur. The absorbent capacity of modified fibers prepared from sulfated fibers is described in Example 3.

Representative methods for preparing a sulfated cellulose polymer are described in Examples 1 and 4.

In one embodiment, the modified polymer is a crosslinked polymer. Crosslinked cellulosic fibers and methods for their preparation are disclosed in U.S. Pat. Nos. 5,437,418 and 5,225,047 issued to Graef et al., expressly incorporated herein by reference.

Crosslinked cellulose fibers can be prepared by treating fibers with a crosslinking agent. Suitable crosslinking agents useful in producing the polymer are generally soluble in water and/or alcohol. Suitable cellulosic fiber crosslinking agents include aldehyde, dialdehyde, and related derivatives (e.g., formaldehyde, glyoxal, glutaraldehyde, glyceraldehyde), and urea-based formaldehyde addition products (e.g., N-methylol compounds). See, for example, U.S. Pat. Nos. 3,224,926; 3,241,533; 3,932,209; 4,035,147; 3,756,913; 4,689,118; 4,822,453; 3,440,135, issued to Chung; U.S. Pat. No. 4,935,022, issued to Lash et al.; U.S. Pat. No. 4,889,595, issued to Herron et al.; U.S. Pat. No. 3,819,470, issued to Shaw et al.; U.S. Pat. No. 3,658,613, issued to Steiger et al.; and U.S. Pat. No. 4,853,086, issued to Graef et al., all of which are expressly incorporated herein by reference in their entirety. Cellulosic fibers can also be crosslinked by carboxylic acid crosslinking agents including polycarboxylic acids. U.S. Pat. Nos. 5,137,537; 5,183,707; and 5,190,563, describe the use of C2–C9 polycarboxylic acids that contain at least three carboxyl groups (e.g., citric acid and oxydisuccinic acid) as crosslinking agents.

Suitable urea-based crosslinking agents include methylolated ureas, methylolated cyclic ureas, methylolated lower alkyl substituted cyclic ureas, methylolated dihydroxy cyclic ureas, dihydroxy cyclic ureas, and lower alkyl substituted cyclic ureas. Specific preferred urea-based crosslinking agents include dimethylol urea (DMU, bis[N-hydroxymethyl]urea), dimethylolethylene urea (DMEU, 1,3-dihydroxymethyl-2-imidazolidinone), dimethyloldihydroxyethylene urea (DMDHEU, 1,3-dihydroxymethyl-4,5-dihydroxy-2-imidazolidinone), dimethylolpropylene urea (DMPU), dimethylolhydantoin (DMH), dimethyldihydroxy urea (DMDH-U), dihydroxyethylene urea (DHEU, 4,5-dihydroxy-2-imidazolidinone), and dimethyldihydroxyethylene urea (DMeDHEU, 4,5-dihydroxy-1,3-dimethyl-2-imidazolidinone).

Suitable polycarboxylic acid crosslinking agents include citric acid, tartaric acid, malic acid, succinic acid, glutaric acid, citraconic acid, itaconic acid, tartrate monosuccinic acid, maleic acid, 1,2,3-propane tricarboxylic acid, 1,2,3,4-butanetetracarboxylic acid, all-cis-cyclopentane tetracarboxylic acid, tetrahydrofuran tetracarboxylic acid, 1,2,4,5-benzenetetracarboxylic acid, and benzenehexacarboxylic acid. Other polycarboxylic acids crosslinking agents include polymeric polycarboxylic acids such as poly(acrylic acid), poly(methacrylic acid), poly(maleic acid), poly (methylvinylether-co-maleate) copolymer, poly (methylvinylether-co-itaconate) copolymer, copolymers of acrylic acid, and copolymers of maleic acid. The use of polymeric polycarboxylic acid crosslinking agents such as polyacrylic acid polymers, polymaleic acid polymers, copolymers of acrylic acid, and copolymers of maleic acid is described in U.S. Pat. No. 5,998,511, assigned to Weyerhaeuser Company and expressly incorporated herein by reference in its entirety.

Other suitable crosslinking agents include diepoxides such as, for example, vinylcyclohexene dioxide, butadiene dioxide, and diglycidyl ether; sulfones such as, for example, divinyl sulfone, bis(2-hydroxyethyl)sulfone, bis(2-chloroethyl)sulfone, and disodium tris(β-sulfatoethyl) sulfonium inner salt; and diisocyanates.

Mixtures and/or blends of crosslinking agents can also be used.

For embodiments of the polymer that are crosslinked with a crosslinking agent, a catalyst can be used to accelerate the crosslinking reaction. Suitable catalysts include acidic salts, such as ammonium chloride, ammonium sulfate, aluminum chloride, magnesium chloride, and alkali metal salts of phosphorous-containing acids.

The amount of crosslinking agent applied to the polymer is suitably the amount necessary to render the polymer substantially insoluble in water. The amount of crosslinking agent applied to the polymer will depend on the particular crosslinking agent and is suitably in the range of from about 0.01 to about 8.0 percent by weight based on the total weight of polymer. In one embodiment, the amount of crosslinking agent applied to the polymer is in the range from about 0.20 to about 5.0 percent by weight based on the total weight of polymer.

The polymer of the invention has a liquid absorbent capacity of at least about 20 g/g as measured by the centrifuge capacity test described in Example 3. In one embodiment, the modified polymer has a capacity of at least about 10 g/g. In another embodiment, the polymer has a capacity of at least about 15 g/g, and in a further embodiment, the polymer has a capacity of at least about 20 g/g. The absorbent capacity of representative polymers formed in accordance with the present invention is described in Example 3.

In another aspect of the invention, a method for manufacturing a superabsorbent polymer is provided. In one embodiment of the method, cellulosic fibers are sulfated by reacting the fibers with a sulfating agent.

For effective sulfation, cellulosic fibers, including dried fibers, can be swelled prior to sulfation using a swelling agent. Suitable swelling agents include, for example, water, glacial acetic acid, acetic anhydride, zinc chloride, sulfuric acid, sulfur trioxide, and ammonia. The fibers can be swelled by mixing the fibers with the swelling agent followed by removing excess swelling agent prior to reacting the fibers with the sulfating agent.

Thus, in another embodiment, the present invention provides a method for making a superabsorbent polymer that includes the steps of swelling cellulosic fibers, including dry fibers, with a swelling agent; separating excess swelling agent from the swelled fibers; reacting the swelled fibers with a sulfating agent; separating excess sulfating agent from the fibers; and at least partially neutralizing the sulfated fibers to provide sulfated cellulosic fibers.

The polymer of the invention can be provided in particle form by dissolving the sulfated polymer formed in the sulfation step in an aqueous medium followed by precipitation of the polymer from the medium. Precipitation of the polymer from the aqueous medium can be achieved by diluting the aqueous medium containing the polymer with a miscible solvent in which the polymer has a low solubility. The polymer particles prepared by this method is referred to as "regenerated" polymer particle because the polymer particle is produced by precipitation from a polymer solution. Precipitation of the polymer can be achieved using a non-aqueous material, such as alcohol (e.g. isopropanol) or a salt. A method for preparing a regenerated polymer particle is described in Example 4. Alternatively, the polymer may also be recovered (or "regenerated") from solution simply by drying off the water from the aqueous solution.

As noted above, in one embodiment, the polymer of the invention is a sulfated and crosslinked polymer. Accordingly, sulfated polymers prepared as described above can be further crosslinked with a crosslinking agent to provide the superabsorbent polymer. A representative method for making a sulfated and crosslinked superabsorbent polymer is described in Example 2.

The polymers of the invention can be incorporated into a personal care absorbent product. The polymers can be formed into a composite for incorporation into a personal care absorbent product. Composites can be formed from the polymer alone or by combining the polymer with other materials, including fibrous materials, binder materials, other absorbent materials, and other materials commonly employed in personal care absorbent products. Suitable fibrous materials include synthetic fibers, such as polyester, polypropylene, and bicomponent binding fibers; and cellulosic fibers, such as fluff pulp fibers, crosslinked cellulosic fibers, cotton fibers, and CTMP fibers. Suitable absorbent materials include natural absorbents, such as sphagnum moss, and synthetic superabsorbents such as polyacrylates (e.g., SAPs).

Absorbent composites derived from or that include the polymers of the invention can be advantageously incorporated into a variety of absorbent articles such as diapers including disposable diapers and training pants; feminine care products including sanitary napkins, and pant liners; adult incontinence products; toweling; surgical and dental sponges; bandages; food tray pads; and the like. Thus, in another aspect, the present invention provides absorbent composites, constructs, and absorbent articles that include the polymer.

The superabsorbent polymer of the invention can be incorporated as an absorbent core or storage layer into a personal care absorbent product such as a diaper. The composite can be used alone or combined with one or more other layers, such as acquisition and/or distribution layers, to provide useful absorbent constructs.

Figure 2:
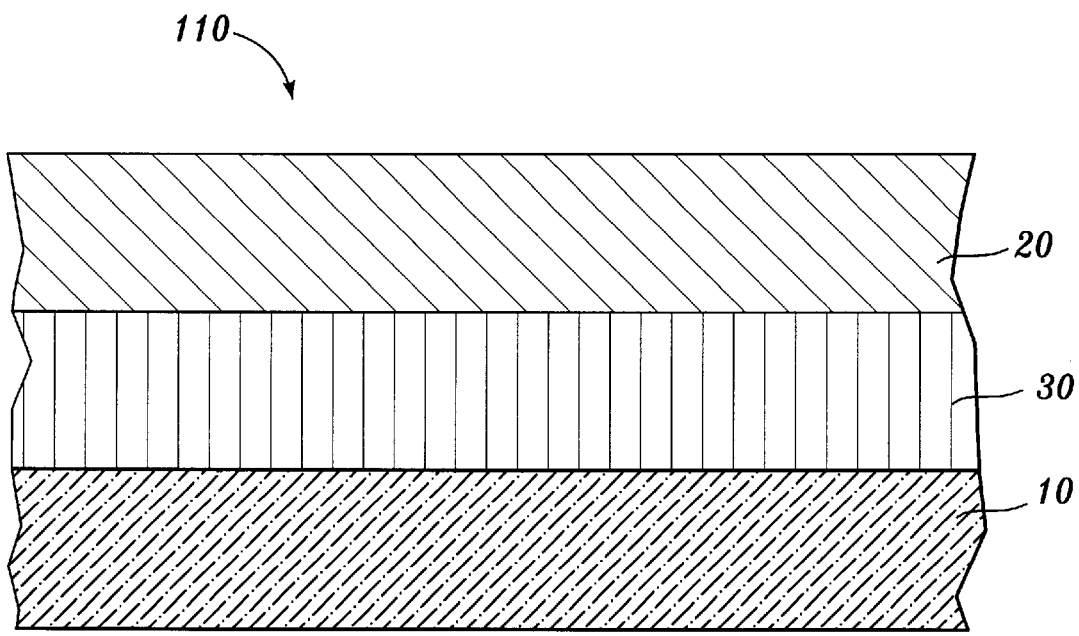
FIG. 2 is a cross sectional view of an absorbent construct incorporating a representative polymer of the invention and having acquisition and distribution layers.

Representative absorbent constructs incorporating an absorbent composite that includes a polymer of the invention are shown in FIGS. 1 and 2. Referring to FIG. 1, construct 100 includes composite 10 (i.e., a composite that includes a polymer of the invention) employed as a storage layer in combination with an upper acquisition layer 20.

In addition to the construct noted above that includes the combination of absorbent composite and acquisition layer, further constructs can include a distribution layer intermediate the acquisition layer and composite. FIG. 2 illustrates construct 110 having intermediate layer 30 (e.g., distribution layer) interposed between acquisition layer 20 and composite 10.

Figure 3A:
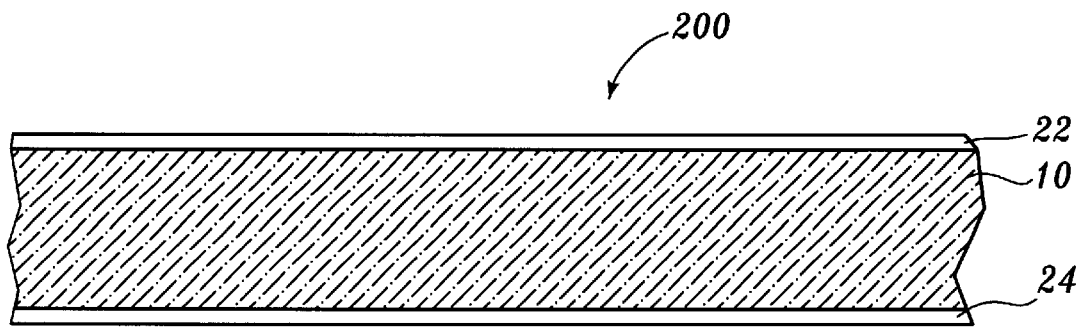
FIGS. 3A–C are cross sectional views of absorbent articles incorporating a composite including representative polymer of the invention and the absorbent constructs illustrated in FIGS. 1 and 2, respectively.
Figure 3B:
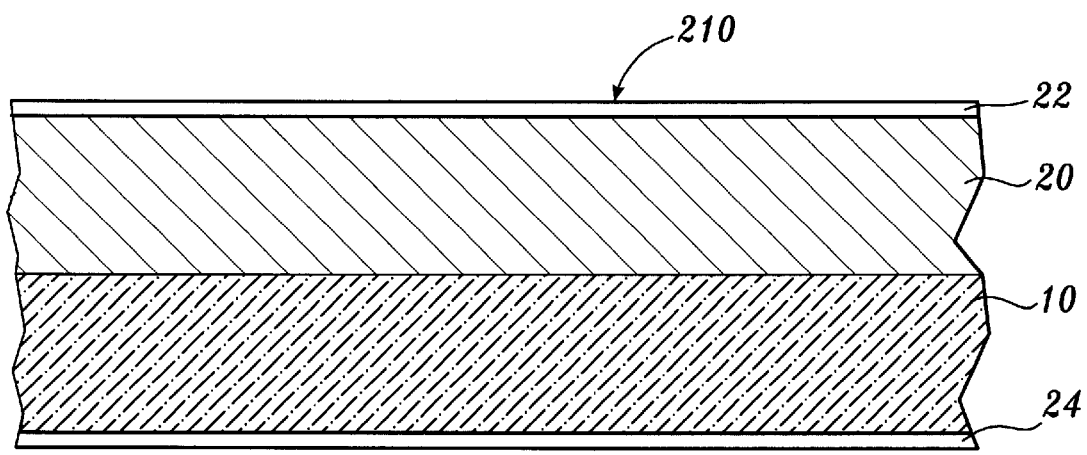
Figure 3C:
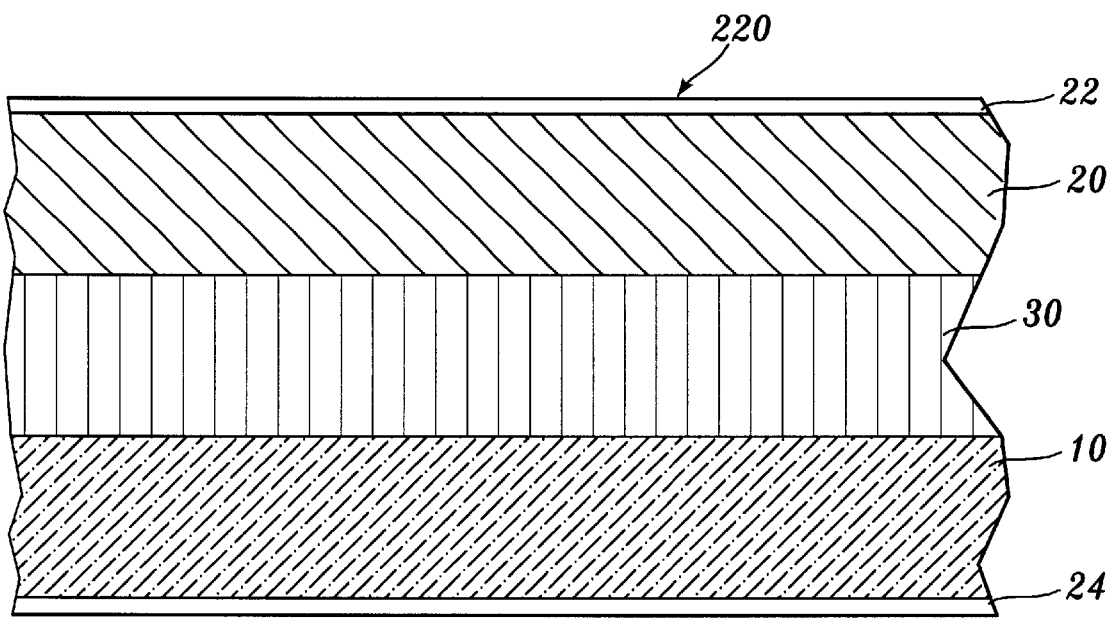

Composite 10 and constructs 100 and 110 can be incorporated into absorbent articles. Generally, absorbent articles 200, 210, and 220 shown in FIGS. 3A–C, include liquid pervious facing sheet 22, liquid impervious backing sheet 24, and a composite 10, construct 100, construct 110, respectively. In such absorbent articles, the facing sheet can be joined to the backing sheet.

It will be appreciated that other absorbent products can be designed incorporating the polymer of the invention and composites that include the polymer.

The following examples are provided for the purposes of illustrating, not limiting, the present invention.

EXAMPLE 1

The Preparation of Sulfated Cellulosic Fibers

In this example, a representative method for forming sulfated cellulosic fibers is described.

Prior to sulfation, the pulp was activated with acetic acid. Ten grams of fiberized bleached kraft southern yellow pine fluff pulp (NB416, Weyerhaeuser Company, Federal Way, Wash.) that had been oven dried at 105° C. was disbursed in 600 mL of glacial acetic acid. The pulp/acid slurry was then placed in a vacuum chamber and the air was evacuated. The slurry was allowed to stand under vacuum for 30 minutes after which time the chamber was repressurized to atmospheric pressure. The slurry was then allowed to stand at ambient conditions for 45 minutes before being resubjected to a vacuum for an additional 30 minutes. After the second application of a vacuum the slurry was again allowed to stand for 45 minutes at atmospheric pressure. The slurry was then poured into a Buchner funnel where the pulp was collected and pressed until the weight of the residual acetic acid was equal to twice the weight of the oven dry pulp (i.e., total weight of the collected pulp was 30 g.) The collected pulp was placed inside a plastic bag and cooled to –10° C. in a freezer.

The sulfation liquor was prepared by mixing 240 g concentrated sulfuric acid with 60 g isopropanol and 0.226 g magnesium sulfate. The liquor was prepared by pouring isopropanol into a beaker that was maintained at 4° C. in an ice bath. Magnesium sulfate was then added to the isopropanol and the mixture chilled to 4° C. Sulfuric acid was weighed into a beaker and separately chilled to 9° C. before being slowly mixed into the isopropanol and magnesium sulfate mixture. The resulting sulfating liquor was then allowed to cool to 4° C.

The cooled acetic acid activated pulp (–10° C.) was stirred into the cooled sulfation liquor (4° C.). The resulting slurry of pulp and sulfation liquor was allowed to react for 35 minutes with constant stirring. After 35 minutes the pulp/sulfation liquor slurry was poured into a Buchner funnel and the sulfated pulp was collected and washed over a vacuum with cooled isopropanol (–10° C.). The collected pulp was then slurried with cooled isopropanol (–10° C.) in a Waring blender and poured back into the Buchner funnel where the pulp was again washed with cooled isopropanol (–10° C.).

The nature and quality of the modified fiber formed in accordance with the invention can depend on the washing step. First, the acid is preferably washed from the pulp as quickly as possible to prevent continued and/or accelerated cellulose degradation. Second, the cool temperature of the pulp is preferably maintained to prevent cellulose degradation. Third, the acid is preferably washed from the pulp as thoroughly as possible before neutralization to prevent the formation of difficult to remove inorganic salts during the neutralization step. These salts can adversely impact modified fiber absorbency.

The washed sulfated pulp was next slurried in cooled isopropanol (–10° C.) and an ethanolic sodium hydroxide solution (saturated solution) was added dropwise until the slurry was neutralized. The slurry was then poured into a Buchner funnel where the neutralized sulfated pulp was washed with room temperature isopropanol. The neutralized sulfated pulp was then agitated to remove any inorganic salts that may have been crusted on the fiber surfaces after which the neutralized sulfated pulp was again washed with isopropanol in a Buchner funnel. Finally the collected sulfated pulp was allowed to air dry.

EXAMPLE 2

The Preparation of Representative Crosslinked Sulfated Cellulosic Fibers

In this example, a representative method for forming crosslinked, sulfated cellulosic fibers is described. Sulfated cellulosic fibers prepared as described in Example 1 were crosslinked wit h a representative crosslinking agent.

A catalyzed urea-formaldehyde system was used to crosslink the sulfated cellulosic fibers. The catalyst included magnesium chloride and the sodium salt of dodecylbenzenesulfonic acid dissolved in 88% ethanol/water. In addition to its primary function, the catalyst solution served as a diluent for the crosslinking agent. The crosslinking agent was obtained by dissolving urea in 37 percent (w/w) aqueous formaldehyde. The crosslinking agent was combined with the catalyst solution and applied to the sulfated fibers. The treated fibers were then cured by placing in a 105° C. oven for 60 minutes.

In the experiment, varying amounts of crosslinking agents were applied to the fibers. The amount of crosslinking agent used ranged from 1–11 percent of the weight of the sulfated fibers and the amount of catalytic diluent used was 250 percent of the weight of the sulfated fibers. The materials and their amounts used in preparing the catalytic diluent and crosslinking agent solutions are shown in Table 1 below.

TABLE 1

Composition of Catalytic Diluent and Crosslinking Agent Solution.

|  | Parts |
|---|---|
| Catalytic Diluent |  |
| Denatured ethanol | 44 |
| Deionized water | 6 |
| Magnesium chloride heptahydrate | 0.214 |
| Dodecylbenzenesulfonic acid, sodium salt | 0.4 |
| Crosslinking Agent Solution |  |
| Urea | 15 |
| 37% (w/w) Formaldehyde | 41 |

EXAMPLE 3

Method for Determining Total Absorptive Capacity and Tea Bag Volume Test

In this example, a method for determining total absorptive capacity and tea bag gel volume test are described. Representative modified fibers, prepared as described in Examples 1 and 2 above, with varying levels of crosslinking agent applied to the fibers were evaluated for absorbent capacity by the total absorptive capacity/tea bag gel volume test described below. Modified fiber absorbent capacity as a function of crosslinking agent applied to the fiber is summarized in Table 2 below.

The preparation of materials, test procedure, and calculations to determine absorbent capacity were as follows.

Preparation of Materials:

1) Tea bag preparation: unroll tea bag material (Dexter #1234T heat-sealable tea bag material) and cut cross ways into 6 cm pieces. Fold lengthwise, outside-to-outside. Heatseal edges ⅛ inch with an iron (high setting), leave top end open. Trim excess from top edge to form a 6 cm×6 cm bag. Prepare 3 tea bags.
2) Label edge with sample identification.
3) Weigh 0.200 g sample (nearest 0.001 g) on tared glassine and record weight. (Weight A, see below.)
4) Fill tea bags with modified fiber sample.
5) Seal top edge of tea bag ⅛ inch with the iron.
6) Weigh and record total weight of tea bag filled with modified fiber sample. Store in sealed plastic bag until ready to test (Weight B, see below).

Test Procedure:

1) Fill container to a depth of at least 2 inch with 1 percent by weight saline solution.
2) Hold tea bag horizontally and distribute modified fiber sample evenly throughout tea bag.
3) Lay tea bag on the liquid surface of the saline solution (begin timing) and allow tea bag to wet-out before submerging the tea bag (about 10 sec.).
4) Soak tea bag for 30 minutes. (NOTE: 2 hours was used in the case of the samples from Example 4.)
5) Remove tea bag from the saline solution with tweezers and clip to a drip rack.
6) Allow tea bag to hang for 3 minutes.
7) Carefully remove tea bag from clip and lightly touch saturated corner of tea bag on blotter to remove excess fluid. Weigh tea bag and record weight (i.e., drip weight) (Weight C, see below).

Calculation of Before Centrifuge Capacity ($Z = g/g$ capacity):

$$Z = (C-B)/A$$

This calculation assumes that the liquid held by the tea bag material is a negligible and reasonably constant factor.

8) Place tea bag on wall of centrifuge by pressing top edge against the wall. Balance centrifuge by placing the tea bags around the centrifuge's circumference.
9) Centrifuge at 2800 rpm for 75 seconds.
10) Remove tea bag from centrifuge, weigh and record tea bag centrifuged weight (Weight D, see below).

Calculation of After Centrifuge Capacity ($Y = g/g$ capacity):

$$Y = (D-B)/A$$

This calculation assumes that the liquid held by the tea bag material is a negligible and reasonably constant factor.

Calculation of Free Liquid Value As a Percentage:

$$\text{Percent free liquid} = ((Z-Y)/Z) \times 100$$

The after centrifuge absorbent capacity (centrifuge capacity, g/g), determined as described above, as a function of sulfation reaction time and crosslinking agent applied to the fiber for representative modified fibers is summarized in Table 2 below.

TABLE 2

Modified Fiber Absorbent Capacity: Crosslinking Level and Sulfation Reaction Time Effect.

| Crosslinking level (percent by weight) | Centrifuge Capacity (g/g) | | |
|---|---|---|---|
|  | 25 minute sulfation | 35 minute sulfation | 45 minute sulfation |
| 1.08 | 13.0 | 12.1 | 7.0 |
| 1.62 | 15.3 | 14.6 | 10.1 |
| 1.94 |  | 17.2 |  |
| 2.27 |  | 15.1 |  |
| 2.48 |  | 17.3 |  |
| 2.27 | 14.7 | 18.0 |  |
| 2.97 |  |  | 11.3 |
| 3.24 |  | 11.9 |  |
| 3.78 | 8.1 | 7.9 | 8.6 |
| 4.00 | 6.6 |  |  |

As shown in Table 2, to a point, absorbent capacity increases with increasing sulfation as all the sulfated fibers have capacities that are higher than one would expect for untreated fiber (only ~1 g/g or so). However, at the point where sulfation results in fiber degradation, absorbent capacity decreases. The results also demonstrate that absorbent capacity also increases with increasing crosslinking to a point. At higher levels of crosslinking, absorbent capacity decreases.

EXAMPLE 4

Representative Superabsorbent Polymer Particle Preparation Method

In this example, a method for preparing a representative superabsorbent cellulosic polymer particle is described. In the method, the polymer is prepared by first sulfating cellulosic pulp followed by dissolving in water and then precipitating the sulfated cellulosic pulp to provide a superabsorbent cellulosic polymer particle.

Cellulosic Pulp Sulfation

Solvent Exchange and Pretreatment of the Never-Dried Pulp. Using a glass stir rod, slurry 50 g (OD basis) of never-dried FR-416 pulp (ca. 25% solids) with 2.7 L of glacial acetic acid in a glass beaker. Allow the acid/pulp slurry to stand for 30 min. Drain and press the slurry over vacuum in the Buchner funnel. Using a glass stir rod, reslurry the filter pad with 2.7 L of glacial acetic acid in a glass beaker. Allow the acid/pulp slurry to stand for 30 min. Drain and press the slurry over vacuum in the Buchner funnel. Using a glass stir rod, reslurry the filter pad with 2.7 L of glacial acetic acid in a glass beaker. Allow the acid/pulp slurry to stand for 30 min. Drain the slurry over vacuum in the Buchner funnel and press the filter pad until the weight of the residual acetic acid is equal to about three times the oven dry weight of the pulp. The total weight of the filter pad will be about 200 g, 50 g of which will be accounted for by the mass of the pulp with the remaining 150 g resulting from residual acetic acid. Shred the filter pad into a ZIPLOC bag and chill to −10° C. in the freezer.

Preparation of the Sulfation Liquor. Place a Hobart mixer and the heat exchanger into an insulated cooling chest. Pour propylene glycol into the insulated cooling chest until all but the top 2 inches of the mixer bowl is submerged. Connect a heat exchanger to the a Julabo FPW55-SP water-cooled ultra-low refrigerated circulator. Fill the tank of the circulator with Baysilone Fluid M3 (a polydimethylsiloxane manufactured by GE Bayer Silicones and distributed by Julabo as Thermal HY). Program the desired temperature into the circulator and start the unit. In this example a temperature of −10° C. was used. Wait for the propylene glycol in the insulated cooling chest to reach the programmed temperature. Pour 300 g of −10° C. isopropanol into the bowl of the mixer. Add 1.13 g of magnesium sulfate to the isopropanol. Slowly stir 1,200 g of 9° C. concentrated sulfuric acid into the isopropanol. Allow the sulfation liquor to cool to the desired reaction temperature. The ratios of the components in the sulfation liquor will be: 4 parts concentrated sulfuric acid, 1 part isopropanol, and 0.004 parts magnesium sulfate.

Sulfation Reaction. Route the mixer's power supply through a rheostat. With the rheostat set at zero switch the mixer on to its lowest setting. Dial up the rheostat until the mixer blade is turning slowly. Feed the shredded −10° C. acetic acid activated FR-416 pulp into the running mixer at a rate that will not overload the mixer, yet is not so slow as to cause the sulfation time of the first pulp in to be significantly different from that of the last pulp in. Maintain the appropriate reaction temperature and allow the pulp to react for the time indicated in Table 3 while undergoing constant stirring. The weight of the sulfation liquor will be 30 times that of the solvent exchanged, never-dried FR-416 pulp being sulfated (not including the weight of the residual acetic acid.)

Filtration and Washing of the Sulfated Pulp. Upon completion of the sulfation reaction, pour the pulp/sulfation liquor slurry into a Buchner funnel and remove as much sulfation liquor from the pulp as possible. Pour 3 L of −10° C. isopropanol through the filter pad to wash away what acid could not be physically removed from the pulp. Disintegrate the filter pad in the Waring blender and pour the resultant slurry into a Buchner funnel. Pour 3 L of −10° C. isopropanol through the filter pad.

There are four important factors in the washing stage. Firstly, to avoid an excessive generation of heat via the mixing of the wash isopropanol with an overabundance of sulfuric acid, as much sulfation liquor as possible should be expressed from the pulp prior to washing. Secondly, the acid must be washed from the pulp as quickly as possible to prevent continued and accelerated degradation to the cellulose. Thirdly, the temperature of the pulp should not be allowed to rise because the cellulose may be extensively damaged. Fourthly, the acid must be washed out as thoroughly as possible before neutralization to prevent the formation of difficult to remove inorganic salts, which would ultimately have a negative impact on the absorbency of the resultant polymer.

Neutralization of the Cellulose Sulfate. Using a pneumatic powered mixer, slurry the washed cellulose sulfate with −10° C. isopropanol in the 4 L plastic beaker. Maintain stirring while adding a saturated ethanolic sodium acetate solution to the slurry dropwise with a burette until a pH of 7 is attained. Drain and press the slurry over vacuum in the Buchner funnel. Agitate the sodium cellulose sulfate in room temperature isopropanol with the Waring blender to remove any inorganic salts that may have crusted on the fiber surfaces. Drain and press the slurry over vacuum in the Buchner funnel. Wash the filter pad with room temperature isopropanol. Shred the filter pad and allow the sodium cellulose sulfate to air dry in a fume hood.

TABLE 3

Representative Polymer Sulfation Reaction Times.

| Sample Number | Sulfation Reaction Time (mins) |
|---|---|
| A | 180 |
| B | 180 |
| C | 240 |

Sodium Cellulose Sulfate Polymer Precipitation

To 13 g water, add 1 gm of the neutralized cellulose sulfate sample prepared as described above. Stir to dissolve the fiber. Stir periodically until complete dissolution is obtained (typically 1–24 hours). Add about 125 ml of isopropanol to the cellulose sulfate solution to precipitate the polymer. Mix well with a small plastic spatula and then pull the precipitated material apart to form small (from about 5 mm to about 10 mm in largest dimension) sized, elongated pieces of precipitate. Filter excess solvent off in a Buchner funnel. Add an additional 125 mL isopropanol to the precipitate as an additional wash. Filter again. Dry the precipitate at 105° C. for 60 minutes in a laboratory fan oven. The free swell and centrifuge capacities were determined as described above in Example 3. The capacities before centrifuge (See Z above), capacities after centrifuge (see Y above), and Free Liquid Value (percent free liquid) for representative polymers prepared as described above are summarized in Table 4 below.

It should be noted in this Example4, in contrast to Example 2, that no crosslinking agent was used in preparing the superabsorbent polymer particles.

TABLE 4

Representative Polymer Particle Absorbent Capacities.

| Sample Number | Z before centrifuge capacity (g/g) | Y after centrifuge capacity(g/g) | Free Liquid Value (%) |
|---|---|---|---|
| A | 32.42[a] | 23.86[a] | 26[a] |
| B | 32.25 | 23.91 | 26 |
| C | 33.02[a] | 24.04[a] | 27[a] |

[a]mean of two replicates.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A cellulose sulfate superabsorbent polymer having a Free Liquid Value less than about 40 percent and an absorptive capacity of at least about 20 g/g.

2. The polymer of claim 1 having a Free Liquid Value less than about 30 percent.

3. The polymer of claim 1, wherein the polymer is a crosslinked polymer.

4. The polymer of claim 1, wherein the polymer is a regenerated polymer.

5. A regenerated, cellulose sulfate superabsorbent polymer having a Free Liquid Value less than about 40 percent.

6. The polymer of claim 5 having a Free Liquid Value less than about 30 percent.

7. The polymer of claim 5, wherein the polymer is a crosslinked polymer.

* * * * *